(12) United States Patent
Matsumura (10) Patent No.: US 10,916,402 B2
(45) Date of Patent: Feb. 9, 2021

(54) ELECTRON BEAM IRRADIATION DEVICE AND ELECTRON BEAM IRRADIATION METHOD

(71) Applicant: HAMAMATSU PHOTONICS K.K., Hamamatsu (JP)

(72) Inventor: Tatsuya Matsumura, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 339 days.

(21) Appl. No.: 16/067,872

(22) PCT Filed: Nov. 1, 2016

(86) PCT No.: PCT/JP2016/082464
§ 371 (c)(1),
(2) Date: Jul. 3, 2018

(87) PCT Pub. No.: WO2017/119180
PCT Pub. Date: Jul. 13, 2017

(65) Prior Publication Data
US 2020/0266024 A1    Aug. 20, 2020

(30) Foreign Application Priority Data

Jan. 8, 2016 (JP) .................... 2016-002726

(51) Int. Cl.
*H01J 37/141* (2006.01)
*H01J 37/06* (2006.01)
(Continued)

(52) U.S. Cl.
CPC ............ *H01J 37/141* (2013.01); *A61L 2/087* (2013.01); *H01J 37/06* (2013.01); *H01J 37/3007* (2013.01)

(58) Field of Classification Search
CPC ...... H01J 37/141; H01J 37/06; H01J 37/3007; A61L 2/087
(Continued)

(56) References Cited

U.S. PATENT DOCUMENTS 7,520,108 B2   4/2009  Kristiansson et al.
8,110,974 B2   2/2012  Matsumura
(Continued)

FOREIGN PATENT DOCUMENTS

CN       103596596 A    2/2014
DE       1 010 201 B    6/1957
(Continued)

OTHER PUBLICATIONS

International Preliminary Report on Patentability dated Jul. 19, 2018 for PCT/JP2016/082464.

*Primary Examiner* — Nicole M Ippolito
(74) *Attorney, Agent, or Firm* — Faegre Drinker Biddle & Reath LLP (57) ABSTRACT

An electron beam irradiation device includes: an electron beam generation part; a housing part that provides a vacuum space in which the electron beam generation part is accommodated; an electron beam guide part in which a base end side is connected to the housing part and communicates with the vacuum space, in which a tip end side is provided with a long tubular member capable of being inserted into a container via a mouth portion of the container, and in which the electron beams pass through an inside; an electron beam emission window which is provided on the tip end side of the electron beam guide part; and an adjustment part that adjusts a trajectory of the electron beams in the electron beam guide part. The adjustment part is disposed on the base end side of the electron beam guide part on an outside of the vacuum space.

13 Claims, 4 Drawing Sheets

(51) Int. Cl.
*H01J 37/30* (2006.01)
*A61L 2/08* (2006.01)

(58) Field of Classification Search
USPC ............ 250/396 ML, 453.11, 454.11, 455.11
See application file for complete search history.

(56) References Cited

U.S. PATENT DOCUMENTS

| | | |
|---|---|---|
| 2007/0283667 A1 | 12/2007 | Kristiansson et al. |
| 2009/0134338 A1* | 5/2009 | Eguchi .................... A61L 2/087 |
| | | 250/396 R |
| 2011/0012032 A1* | 1/2011 | Bufano .................... G21K 5/02 |
| | | 250/492.3 |
| 2015/0336701 A1* | 11/2015 | Eidebakken ............ A61L 2/087 |
| | | 53/426 |

FOREIGN PATENT DOCUMENTS

| | | |
|---|---|---|
| DE | 102013101371 A1 | 8/2014 |
| EP | 2528064 A1 | 11/2012 |
| JP | H07-18299 U | 3/1995 |
| JP | 2007-240454 A | 9/2007 |
| JP | 2007-242556 A | 9/2007 |
| JP | 2008-128971 A | 6/2008 |
| JP | 2008-128977 A | 6/2008 |
| JP | 2008-128978 A | 6/2008 |
| JP | 2012-55556 A | 3/2012 |
| JP | 2013-129453 A | 7/2013 |
| JP | 2013-160721 A | 8/2013 |
| JP | 2014-134548 A | 7/2014 |
| JP | 5774156 B2 | 9/2015 |
| WO | WO-2007/095205 A2 | 8/2007 |
| WO | WO-2014/175065 A1 | 10/2014 |

* cited by examiner

ELECTRON BEAM IRRADIATION DEVICE AND ELECTRON BEAM IRRADIATION METHOD

TECHNICAL FIELD

An aspect of the invention relates to an electron beam irradiation device and an electron beam irradiation method.

BACKGROUND ART

In the related art, there is known an electron beam irradiation device including an electron beam generation part that generates an electron beam, a housing part that provides a vacuum space for accommodating the electron beam generation part, an electron beam guide part in which one end side is connected to the housing part to communicate with the vacuum space, and an electron beam emission window that is provided on the other end side of the electron beam guide part and from which the electron beams are emitted. In the electron beam irradiation device, to perform sterilization of an inner surface of a container, for example, a bottle, and the like, it is required to efficiently irradiate the inner surface of the bottle with electron beams. In this regard, for example, Patent Literature 1 discloses an electron beam irradiator including an electron beam guide part (nozzle) which is constituted by a long tubular member and in which a tip end side of the electron beam guide part has a configuration capable of being inserted into a bottle through a mouth portion (opening portion) of the bottle.

CITATION LIST

Patent Literature

Patent Literature 1: Japanese Patent No. 5774156

SUMMARY OF INVENTION

Technical Problem

In the related art described in Patent Literature 1, the electron beam generation part is formed inside the vacuum space, and dimension fitting and positioning thereof are performed so that the electron beams generated pass through the inside of the electron beam guide part having a configuration capable of being inserted into the bottle, and are emitted from the electron beam emission window. In this case, a trajectory of the electron beams until reaching the electron beam emission window from the electron beam generation part is greatly influenced by an emission state of the electron beams from the electron beam generation part, and a positional relationship between the electron beam generation part and the electron beam emission window. According to this, the trajectory of the electron beams are likely to be influenced by assembly accuracy and fixing accuracy of the electron beam generation part. If there is a problem relating to the assembly accuracy and the fixing accuracy, there is a possibility that deviation from an intended trajectory may occur. Particularly, in a case where the electron beams are emitted through the electron beam guide part that is a long tubular member capable of being inserted into the bottle, from the viewpoint of propagation through a narrow and long space, a slight trajectory deviation of the electron beams may lead to, for example, incidence to an inner wall of the electron beam guide part and the like before reaching the electron beam emission window.

According to this, there is a high possibility that an electron beam amount reaching to the electron beam emission window is greatly reduced. That is, when stably emitting the electron beams from the electron beam emission window by using the electron beam generation part, high accuracy is necessary in regard to the processing, assembly, and disposition of the electron beam generation part. Accordingly, there is a concern that it is difficult to stably emit the electron beams from the electron beam emission window on a tip end side of the electron beam guide part.

An object of one aspect of the invention is to stably emit electron beams from an electron beam emission window on a tip end side of an electron beam guide part in an electron beam irradiation device that includes the electron beam guide part including a long tubular member capable of being inserted into a container from a mouth portion of the container and an electron beam irradiation method using the electron beam irradiation device.

Solution to Problem

According to one aspect of the invention, there is provided an electron beam irradiation device including: an electron beam generation part that generates electron beams; a housing part that provides a vacuum space in which the electron beam generation part is accommodated; an electron beam guide part in which a base end side is connected to the housing part and communicates with the vacuum space, in which a tip end side is provided with a long tubular member capable of being inserted into a container via a mouth portion of the container, and in which the electron beams generated in the electron beam generation part pass through an inside; an electron beam emission window which is provided on the tip end side of the electron beam guide part, and through which the electron beams are emitted; and an adjustment part that adjusts a trajectory of the electron beams in the electron beam guide part. The adjustment part is disposed on the base end side of the electron beam guide part on an outside of the vacuum space.

In the electron beam irradiation device, the electron beam guide part includes the long tubular member capable of being inserted into the container via the mouth portion of the container on the tip end side. In addition, the adjustment part is disposed on the base end side of the electron beam guide part on an outside of the vacuum space. The trajectory of the electron beam is adjusted in the electron beam guide part by the adjustment part. Accordingly, high accuracy relating to processing, assembly, and disposition of the electron beam generation part is not necessary, and it is possible to allow the electron beams generated in the electron beam generation part to reliably reach the electron beam emission window on the tip end side of the electron beam guide part, and emitting the electron beams therefrom. That is, in the electron beam irradiation device including the electron beam guide part provided with the long tubular member capable of being inserted into the container from the mouth portion of the container, it is possible to stably emit the electron beams from the electron beam emission window on the tip end side of the electron beam guide part.

In the electron beam irradiation device according to the aspect of the invention, the adjustment part may be an electromagnetic coil. In this case, it is possible to finely adjust the trajectory of the electron beams in the electron beam guide part by the adjustment part, and thus it is possible to emit the electron beams from the electron beam emission window on the tip end side of the electron beam guide part in a more stable manner.

The electron beam irradiation device according to the aspect of the invention may further include a focusing part that is disposed on an outside the vacuum space, and controls focusing of the electron beams in the electron beam guide part. In this case, the focusing control of the electron beams in the electron beam guide part is reliably performed by the focusing part, and thus it is possible to emit the electron beams from the electron beam emission window on the tip end side of the electron beam guide part in a more stable manner.

In the electron beam irradiation device according to the aspect of the invention, the focusing part may be an electromagnetic coil. In this case, it is possible to finely adjust the focusing of the electron beams in the electron beam guide part by the focusing part, and thus it is possible to emit the electron beams from the electron beam emission window on the tip end side of the electron beam guide part in a more stable manner.

In the electron beam irradiation device according to the aspect of the invention, the focusing part may focus the electron beams so that a focusing point is not formed on the inside of the electron beam guide part. In a case where the focusing point of the electron beams exists at the inside of the electron beam guide part, there is a concern that the focusing point may be located on the electron beam emission window, for example, due to an influence of discharging, and thus there is a concern that the electron beam emission window may be broken due to concentration of the electron beams. In contrast, since the electron beams are focused by the focusing part so that the focusing point is not formed on the inside of the electron beam guide part, it is possible to reduce possibility of the breakage of the electron beam emission window, and thus it is possible to emit the electron beams from the electron beam emission window on the tip end side of the electron beam guide part in a more stable manner.

In the electron beam irradiation device according to the aspect of the invention, the adjustment part may be disposed closer to the base end side of the electron beam guide part than the focusing part. In this configuration, the electron beams, which propagate toward the electron beam emission window at the inside of the electron beam guide part, are subjected to the focusing control in the focusing part after the trajectory is adjusted in the adjustment part. Accordingly, even in a case where a deviation of the trajectory of the electron beam from the electron beam generation part is great, it is possible to adjust the trajectory by the focusing part so that the focusing control of the electron beam can be reliably performed, and thus it is possible to emit the electron beams from the electron beam emission window on the tip end side of the electron beam guide part in a more stable manner.

In the electron beam irradiation device according to the aspect of the invention, the focusing part may be disposed closer to the base end side of the electron beam guide part than the adjustment part. In this configuration, the trajectory of the electron beams, which propagate at the inside of the electron beam guide part toward the electron beam emission window, is adjusted in the adjustment part after the electron beams are subjected to the focusing control in the focusing part. Accordingly, even in a case where divergence of the electron beams from the electron beam generation part is great, the trajectory of the electron beams is adjusted after focusing the divergence in advance, and thus it is possible to easily adjust the trajectory of the electron beams in the adjustment part. Accordingly, it is possible to emit the electron beams from the electron beam emission window on the tip end side of the electron beam guide part in a more stable manner.

In the electron beam irradiation device according to the aspect of the invention, the electron beam generation part may be configured so that an electron beam amount of the electron beams emitted from the electron beam emission window of the tip end side of the electron beam guide part is reduced in a case where the adjustment part is not provided in comparison to a case where the adjustment part is provided. In this configuration, in a case where the adjustment part is not provided, even in a state in which the electron beam amount of the electron beams emitted from the electron beam emission window is small, it is possible to obtain a sufficient electron beam amount through adjustment of the trajectory of the electron beams in the adjustment part.

According to another aspect of the invention, there is provided an electron beam irradiation device including: an electron beam generation part that generates electron beams; a housing part that provides a vacuum space in which the electron beam generation part is accommodated; an electron beam guide part in which a base end side is connected to the housing part and communicates with the vacuum space, in which a tip end side is provided with a long tubular member capable of being inserted into a container via a mouth portion of the container, and in which the electron beams generated in the electron beam generation part pass through an inside; an electron beam emission window which is provided on the tip end side of the electron beam guide part, and through which the electron beams are emitted; an adjustment part that adjusts a trajectory of the electron beams in the electron beam guide part; a focusing part that is disposed on an outside the vacuum space, and controls focusing of the electron beams in the electron beam guide part; and a control unit that controls the focusing part. The adjustment part is disposed on the base end side of the electron beam guide part on an outside of the vacuum space, and the focusing part is an electromagnetic coil in which flows a current controlled by the control unit so as to pertain) a focusing control to suppress scattering of the electron beams while focusing the electron beams so that a focusing point is not formed on the inside of the electron beam guide part, and to make an irradiation range of the electron beams on the electron beam emission window be constant.

According to still another aspect of the invention, there is provided an electron beam irradiation method of irradiating an inner surface of a container with electron beams by using an electron beam irradiation device including an electron beam generation part that generates electron beams, a housing part that provides a vacuum space in which the electron beam generation part is accommodated, an electron beam guide part in which a base end side is connected to the housing part and communicates with the vacuum space, in which a tip end side is provided with a long tubular member capable of being inserted into a container via a mouth portion of the container, and in which the electron beams generated in the electron beam generation part pass through an inside, an electron beam emission window which is provided on the tip end side of the tubular member of the electron beam guide part, and through which the electron beams are emitted, an adjustment part that is disposed on the base end side of the electron beam guide part on an outside of the vacuum space, and adjusts a trajectory of the electron beams in the electron beam guide part, and a focusing part that controls focusing of the electron beams in the electron beam guide part. The method includes: a step of generating the electron beams from the electron beam generation part, and adjusting a trajectory of the electron beams passing through the electron beam guide part by the adjustment part while allowing the electron beams to pass through the inside of the electron beam guide part, thereby allowing the electron beams to reach the electron beam emission window and emitting the electron beams therefrom; and a step of setting the electron beams to an emission state, then inserting the tubular member into the inside of the container via the mouth portion of the container, and irradiating the inner surface of the container with the electron beams while constantly varying a relative positional relationship between the container and the electron beam emission window. The irradiating step with the electron beams includes a step of positioning the tip end of the tubular member on the inside of the container, and irradiating a bottom surface of the container with the electron beams. The emitting step includes adjusting the trajectory of the electron beams by the adjustment part to match with the central axis line of the tubular member, and focusing the electron beams by the focusing part so that a focusing point is not formed on the inside of the electron beam guide part.

Advantageous Effects of Invention

According to the aspects of the invention, it is possible to stably emit electron beams from the electron beam emission window on the tip end side of the electron beam guide part in the electron beam irradiation device that includes the electron beam guide part including the long tubular member capable of being inserted into a container from a mouth portion of the container and the electron beam irradiation method using the electron beam irradiation device.

DESCRIPTION OF EMBODIMENTS

Hereinafter, embodiments will be described in detail with reference to the accompanying drawings. In the following description, the same reference numeral will be given to the same or equivalent element, and redundant description will be omitted.

Figure 1:
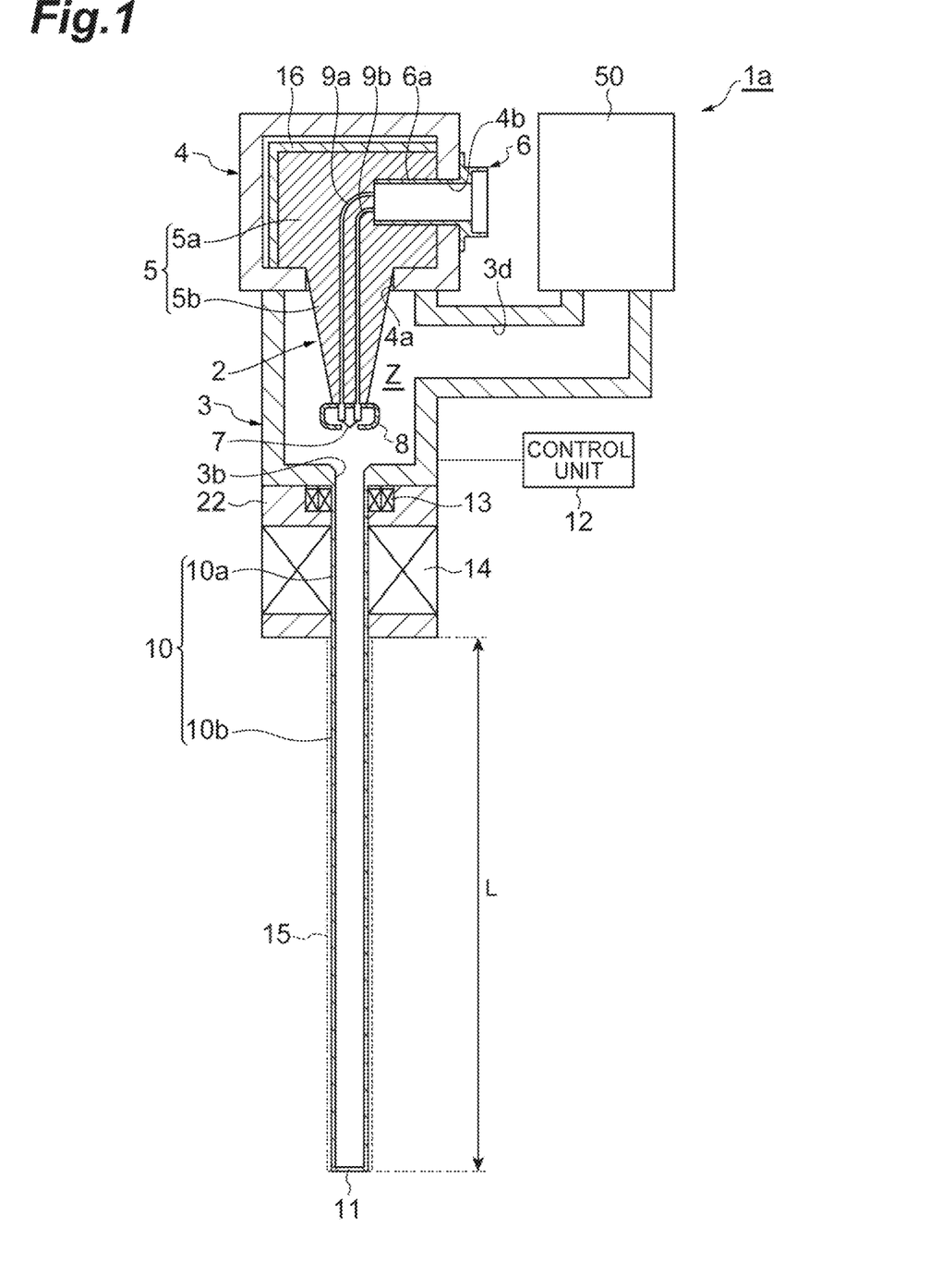
FIG. 1 is a cross-sectional view illustrating an electron beam irradiation device according to a first embodiment.

FIG. 1 is a longitudinal cross-sectional view of an electron beam irradiation device according to a first embodiment. An electron beam irradiation device 1a according to the first embodiment as illustrated in FIG. 1 is used to perform drying, sterilization, surface modification of an irradiation target, and the like by irradiating the irradiation target with electron beams EB. In addition, hereinafter, an electron beam emission side (electron beam emission window 11 side) in which the electron beams EB are emitted by the electron beam irradiation device 1a is set as a front side in the following description.

The electron beam irradiation device 1a includes an electron gun 2, a vacuum container 3, a guide part 10, an electron beam emission window 11, a control unit 12, an adjustment electromagnetic coil 13, and a focusing electromagnetic coil 14. The electron gun 2 is an electron beam generation part that generates electron beams EB which are low-energy electron beams. The electron gun 2 includes a case 4, an insulating block 5, a connector 6, a filament 7, a grid part 8, internal interconnections 9a and 9b, and a conductive member 16.

The case 4 is formed from a conductive material such as a metal. The case 4 accommodates the insulating block 5. The case 4 includes an opening 4a that is connected to a vacuum space Z (to be described later) inside the vacuum container 3, and an opening 4b that is connected to an outer side of the electron beam irradiation device 1a. The opening 4a is a circular opening through which the internal interconnections 9a and 9b pass. The opening 4b is a circular opening for attachment of the connector 6.

The insulating block 5 is formed from an insulating material (for example, an insulating resin such as an epoxy resin, ceramic, and the like). The insulating block 5 insulates a portion (for example, the case 4, and the like) different from the internal interconnections 9a and 9b in the electron gun 2. The insulating block 5 includes a base portion 5a and a convex portion 5b that protrudes from the base portion 5a. The base portion 5a is accommodated in the case 4 to occupy the majority of the inside of the case 4. The convex portion 5b protrudes from the base portion 5a to a front side through the opening 4a, and is exposed from the case 4.

The connector 6 is a high withstand voltage type connector (receptacle) to which power supply voltage is supplied from the outside of the electron beam irradiation device 1a. The connector 6 is attached to a lateral surface of the case 4. The connector 6 is disposed in the opening 4b to penetrate through a side wall of the case 4. In the connector 6, a portion 6a located inside the case 4 is fixed in a state of being embedded in the base portion 5a of the insulating block 5. The connector 6 strongly fixes the insulating block 5 and the case 4. A power supply plug, which holds a tip end of an external interconnection extending from a power supply device (not illustrated), is inserted into the connector 6. In addition, a high voltage necessary in the insulating block 5 may be generated by accommodating a high voltage generation part including a booster circuit at the inside of the insulating block 5 instead of receiving supply of a necessary high voltage through the connector 6 from the external power supply.

The filament 7 is an electron emission member that emits electrons which become the electron beams EB. The filament 7 is formed from a material including tungsten as a main component. The filament 7 is disposed on a front side of the convex portion 5b of the insulating block 5 (in this embodiment, in the vicinity of the tip end of the convex portion 5b). Both ends of the filament 7 are respectively connected to the internal interconnections 9a and 9b which extend to the filament 7 from the connector 6. Accordingly, when the power supply plug is inserted into the connector 6, the both ends of the filament 7 are electrically connected to the power supply device through an external interconnection. When several amperes of current flows through the filament 7, the filament 7 is heated to a temperature of approximately 2500° C., and when a negative voltage as high as negative several tens of kV to negative several hundreds of kV is applied to the filament 7 from another power supply device, the filament 7 emits electrons. The filament 7 is covered with the grid part 8 through which electrons are taken out and which forms an electric field for suppressing diffusion. A predetermined voltage is applied to the grid part 8 through an interconnection (not illustrated). Accordingly, electrons emitted from the filament 7 are emitted as the electron beams EB from a hole formed at a part of the grid part 8.

The internal interconnections 9a and 9b are high-voltage parts to which a high voltage is applied from the power supply device. The internal interconnections 9a and 9b are embedded in the insulating block 5, and thus insulation with the case 4 is secured.

The conductive member 16 is a conductive member that covers a surface of the insulating block 5 on which a gap exists in a space between the surface and the case 4. As the conductive member 16, a thin member such as a conductive film and a conductive tape is used. The conductive member 16 is attached to the insulating block 5 to completely cover a portion of the insulating block 5 which is not in close contact with the case 4. In addition, the conductive member 16 may be a conductive coating, a conductive film, and the like.

The vacuum container 3 is a housing part that provides the vacuum space Z in which the electron gun 2 is accommodated. The vacuum container 3 is formed from a conductive material such as a metal. The vacuum container 3 is formed in a cylindrical shape that extends along an emission direction of the electron beams EB. The vacuum container 3 accommodates and air-tightly seals the filament 7 of the electron gun 2, the grid part 8, and the convex portion 5b of the insulating block 5. In the vacuum container 3, a passage hole 3b is formed at a portion that faces the front side of the electron gun 2. The passage hole 3b is a circular through-hole through which the electron beams EB generated in the electron gun 2 pass. The passage hole 3b communicates with the inside of the guide part 10. The passage hole 3b communicates with the inside of the guide part 10. A vacuum pump 50 is connected to the vacuum container 3 through an exhaust passage 3d. Exhausting of the inside of the vacuum container 3 can be simply performed by the vacuum pump 50.

The guide part 10 is an electron beam guide part that guides the electron beams EB generated in the electron gun 2. The inside of the guide part 10 is hollow, and an internal space thereof constitutes a space in which the electron beams EB generated in the electron gun 2 pass. In this embodiment, the guide part 10 has a cylindrical shape having a uniform inner diameter over an entire length thereof. The guide part 10 includes a base end portion 10a and a rod portion 10b.

The base end portion 10a is a base end side of the guide part 10 and is connected to the vacuum container 3. The internal space of the guide part 10 and the vacuum space Z communicate with each other through the base end portion 10a. The rod portion 10b is a tip end side of the guide part 10 and has a configuration capable of being inserted into a bottle B through a mouth portion Ba of the bottle B that is a container as to be described later. The rod portion 10b is a long tubular member (here, an elongated cylindrical member) that has an outer diameter smaller than a diameter of the vacuum container 3. Specifically, the base end portion 10a is fixed so that the internal space of the guide part 10 is continuous with the passage hole 3b of the vacuum container 3. The rod portion 10b communicates with the base end portion 10a. The rod portion 10b extends along an emission direction of the electron beam EB of the electron gun 2 to be spaced away from the vacuum container 3. In addition, in this embodiment, the base end portion 10a and the rod portion 10b are integrally formed as a long tubular member having an outer diameter that is smaller than a diameter of the vacuum container 3.

The electron beam emission window 11 allows the electron beams EB, which pass through the inside of the guide part 10, to be transmitted therethrough, and emits the electron beams EB toward the outside. The electron beam emission window 11 is provided in the tip end side of the guide part 10. Specifically, the electron beam emission window 11 is provided to vacuum-seal an opening of a tip end portion that is a front side end (an end opposite to the electron gun 2 side) of the rod portion 10b. The electron beam emission window 11 is a thin film type member. The electron beam emission window 11 is a formed from a material (for example, beryllium, titanium, aluminum, and the like) through which the electron beams EB are transmitted. For example, the electron beam emission window 11 is formed in a thickness of 15 μm or less. Here, the electron beam emission window 11 is formed in a thickness of several μm to 10 μm. The electron beam emission window 11 soldered to the rod portion 10b at the tip end of the guide part 10 by using a brazing material. According to this, the electron beam emission window 11 is air-tightly joined to close the opening of the tip end portion of the rod portion 10b. In addition, for example, the electron beam emission window 11 may be joined through welding, or may be held so that the thin film type member can be replaced by a window frame portion having an air-tight holding structure.

For example, the control unit 12 is constituted by one or more computer devices including a processor and a storage device (memory and the like). The control unit 12 operates in accordance with a program stored in the storage device and controls respective parts of the electron beam irradiation device 1a.

The adjustment electromagnetic coil 13 is an adjustment part that adjusts the trajectory of the electron beams EB in the guide part 10. The adjustment electromagnetic coil 13 functions as an electromagnetic lens. The adjustment electromagnetic coil 13 finely adjusts the trajectory (emission axis line) by deflecting a propagation direction of the electron beams EB so that the electron beams EB which pass through the inside of the guide part 10 reach the electron beam emission window 11. For examples, the adjustment electromagnetic coil 13 performs the fine adjustment so that the emission axis line of the electron beams EB approximately matches the central axis line of the guide part 10 (particularly, the rod portion 10b). The adjustment electromagnetic coil 13 is connected to the control unit 12, and a flowing current is controlled by the control unit 12. According to this, the fine adjustment of the trajectory of the electron beams EB is realized.

The adjustment electromagnetic coil 13 is disposed on the base end side (vacuum container 3 side) of the guide part 10 at the outside of the vacuum space Z. More specifically, the adjustment electromagnetic coil 13 is disposed in an annular shape to surround the base end portion 10a at a position on the base end side close to the vacuum container 3 in the base end portion 10a of the guide part 10. The adjustment electromagnetic coil 13 is covered with a holding member 22 and thus a position is held. The holding member 22 is fixed to a front side of the vacuum container 3. The holding member 22 covers the base end portion 10a that is a part (region ranging from the base end to the tip end side by a predetermined distance) of the base end side in the guide part 10. In other words, in this embodiment, in the guide part 10, a portion covered with the holding member 22 becomes the base end portion 10a.

The focusing electromagnetic coil 14 is a focusing part that control focusing of the electron beams EB in the guide part 10. The focusing electromagnetic coil 14 functions as an electromagnetic lens. The focusing electromagnetic coil 14 focuses the electron beams EB which pass through the inside of the guide part 10 (particularly, the rod portion 10b) so as not to form a focusing point. For example, the focusing electromagnetic coil 14 performs a focusing control to suppress scattering of the electron beams EB which propagate to spread along the emission axis line, and to make an irradiation range of the electron beams EB on the electron beam emission window 11 constant. The focusing electromagnetic coil 14 is connected to the control unit 12, and a flowing current is controlled by the control unit 12. According to this, fine adjustment of the focusing control of the electron beams EB is realized.

At the outside of the vacuum space Z, the focusing electromagnetic coil 14 is disposed on a tip end side of the guide part 10 which is further front side in comparison to the adjustment electromagnetic coil 13 (the electron beam emission window 11 side, and a side opposite to the vacuum container 3 side). In other words, the adjustment electromagnetic coil 13 is disposed closer to the base end side of the guide part 10 (electron gun 2 side) than the focusing electromagnetic coil 14. More specifically, the focusing electromagnetic coil 14 is disposed in an annular shape to surround the base end portion 10a at a position adjacent to the front side (tip end side of the guide part 10) with respect to the adjustment electromagnetic coil 13 at the base end portion 10a of the guide part 10. The adjustment electromagnetic coil 13 and the focusing electromagnetic coil 14 are disposed to be arranged in this order along the emission direction of the electron beams EB. A position of the focusing electromagnetic coil 14 is held by the holding member 22 and the focusing electromagnetic coil 14 is covered with the holding member 22.

Figure 2:
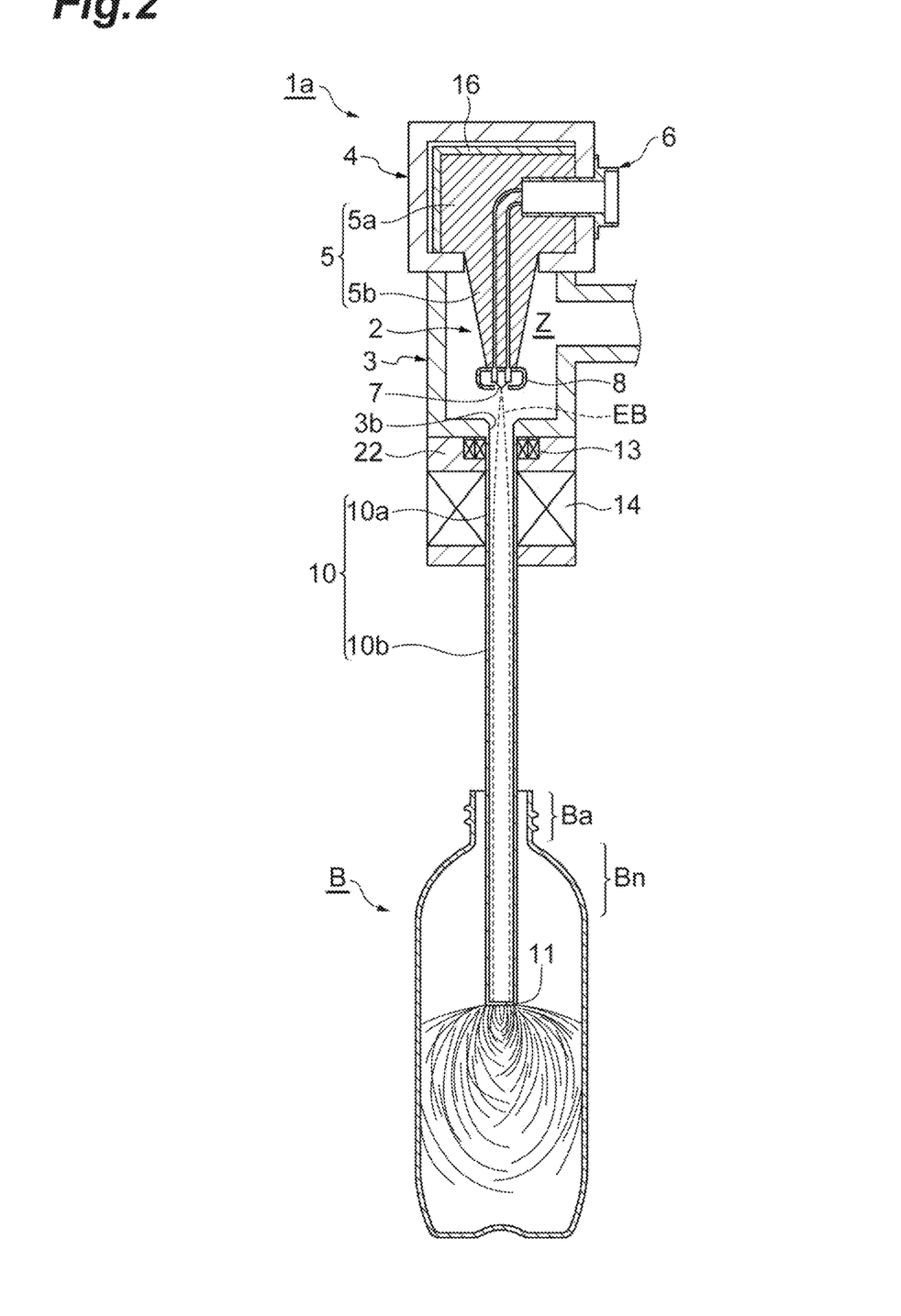
FIG. 2 is a cross-sectional view illustrating the electron beam irradiation device illustrated in FIG. 1.

FIG. 2 is a cross-sectional view illustrating a use state of the electron beam irradiation device illustrated in FIG. 1. As illustrated in FIG. 1 and FIG. 2, the rod portion 10b that is the tip end side of the guide part 10 has a configuration capable of being inserted into the bottle B through the mouth portion Ba of the bottle B that is a container. In order words, in this embodiment, in the guide part 10, a portion, which protrudes from the holding member 22 and has a configuration capable of being inserted into the bottle B through the mouth portion Ba of the bottle B, becomes the rod portion 10b.

In an example illustrated in the drawing, the bottle B is a container including the mouth portion Ba that is an opening portion that is contiguous to a neck portion Bn. An inner diameter of the mouth portion Ba is smaller than an outer diameter of the vacuum container 3 and is larger than an outer diameter of the rod portion 10b. That is, the rod portion 10b has the outer diameter capable of being inserted into the mouth portion Ba of the bottle B along an axis direction of the bottle B. For example, the outer diameter of the rod portion 10b is set to approximately $\phi$18 mm as a dimension capable of being inserted from the mouth portion Ba. A length L of the rod portion 10b, which is an axial length of the portion protruding from the holding member 22 in the guide part 10, is set to a length so that the tip end of the rod portion 10b, which pass through the mouth portion Ba and is located inside the bottle B, can reach the vicinity of the bottom surface of the bottle B so as to irradiate the bottom surface of the bottle B with the electron beams EB. The vicinity of the bottom surface is also referred to as a position close to the bottom surface, a neighborhood of the bottom surface, the periphery of the bottom surface, a position near the bottom surface, or a position within a predetermined distance from the bottom surface. The vicinity of the bottom surface is a position at which the bottom surface of the bottle B is capable of being sufficiently irradiated with the electron beams EB in a case where the tip end of the rod portion 10b is located in the vicinity of the bottom surface.

The length L of the rod portion 10b is set to 300 mm or greater. In this embodiment, the length L of the rod portion 10b is 300 mm to 400 mm. There is no particular limitation to the bottle B that is applied, and all kinds of bottles B are applicable. A size, a material, a shape, an external appearance, a use, and the like of the bottle B are not limited, and various kinds of bottles are applicable. As the bottle B in this embodiment, a beverage PET bottle with a capacity of two liters is applied.

The guide part 10 is formed from a nonmagnetic substance. For example, the guide part 10 is formed from stainless steel, aluminum, oxygen-free copper, and the like. According to this, it is possible to guide a magnetic field, which is formed by the adjustment electromagnetic coil 13 and the focusing electromagnetic coil 14 provided at the periphery of the guide part 10, to the electron beams EB inside the guide part 10. According to this, it is necessary for, particularly, the base end portion 10a in the guide part 10 to be formed from the nonmagnetic substance.

On the other hand, in the guide part 10, an outer surface of the rod portion 10b that is a portion protruding from the holding member 22 (a portion corresponding to the length L as a portion that is exposed to the outside and can be inserted into the bottle B) is covered with a magnetic substance 15. The magnetic substance 15 functions as a magnetic shield. The magnetic substance 15 shields external magnetism such as the Earth's magnetism that reaches the electron beams EB inside the rod portion 10b, and suppresses a deviation of the trajectory of the electron beams EB. In addition, the rod portion 10b may be formed from a magnetic substance instead of additionally covering the rod portion 10b formed from a nonmagnetic substance with the magnetic substance 15.

Description will be given of an operation (electron beam irradiation method) of the electron beam irradiation device 1a of this embodiment which has the above-described configuration.

First, the inside of the vacuum container 3 is evacuated by the vacuum pump 50 to form the vacuum space Z. Then, the filament 7 is electrified to preliminarily heat the filament 7, thereby preparing electron emission. Subsequently, a power supply voltage of negative several tens of kV to negative several hundreds of kV is applied from the power supply device. The power supply voltage is supplied to the filament 7 through the internal interconnections 9a and 9b. In addition, the filament 7 is heated up to a temperature at which a desired tube current value is obtained. In addition, the filament 7 may be directly heated to the temperature at which the desired tube current value is obtained without performing the preliminary heating. Then, electrons are taken out from the filament 7 by the grid part 8, and are emitted to the front side.

The electrons emitted from the filament 7 become the electron beams EB of which diffusion is suppressed by the grid part 8 and which have energy corresponding to the application voltage. The electron beams EB straightly propagate to the front side to spread, and propagate toward the electron beam emission window 11 in the internal space of the guide part 10. At this time, the trajectory of the electron beams EB is finely adjusted by the adjustment electromagnetic coil 13 so that the trajectory thereof matches the central axis line of the guide part 10 (particularly, the rod portion 10b), and the electron beams EB are subjected to a focusing control by the focusing electromagnetic coil 14 so that a focusing point is not formed on the inside of the guide part 10 (particularly, the rod portion 10b).

The electron beams EB of which the trajectory is finely adjusted and which is subjected to the focusing control reach the electron beam emission window 11, are transmitted through the electron beam emission window 11, and are emitted to the outside of the electron beam irradiation device 1a. After the electron beams EB enter an emission state, the rod portion 10b of the guide part 10 on the tip end side is inserted into the bottle B through the mouth portion Ba, and the electron beam emission window 11 at the tip end of the rod portion 10b is located at a desired position inside the bottle B. As a result, the inner surface of the bottle B is efficiently irradiated with the electron beams EB, and the inner surface of the bottle B is sterilized. In addition, a relative positional relationship between the bottle B and the electron beam emission window 11 is controlled to constantly vary so as to suppress deterioration due to excessive irradiation of a local site of the bottle B with the electron beams EB.

Here, it is necessary for a portion, from which the electron beams EB are emitted, to be inserted into the bottle B to efficiently irradiate the inner surface of the bottle B with the electron beams EB. In this regard, as a basic structure in the guide part 10, the electron beam irradiation device 1a includes the elongated rod portion 10b capable of being inserted into the bottle B from the mouth portion Ba of the bottle B. According to this, it is necessary to allow the electron beams EB emitted from the electron gun 2 to efficiently reach the electron beam emission window 11 on a tip end side after passing through an elongated internal space of the elongated rod portion 10b.

On the other hand, in a case where the electron gun 2 in the electron beam irradiation device 1a is not provided with the adjustment electromagnetic coil 13, the electron gun 2 has a configuration in which an electron beam amount emitted from the electron beam emission window 11 is further reduced in comparison to a case where the electron gun 2 is provided with the adjustment electromagnetic coil 13. In other words, the electron gun 2 has a configuration in which the electron beam amount that cannot reach the electron beam emission window 11 further increases in comparison to the case where the adjustment electromagnetic coil 13 is provided. Specifically, in a case where the electron gun 2 is not provided with the adjustment electromagnetic coil 13, if processing, assembly, disposition, and the like of the electron gun 2 are not performed with high accuracy, there is a high possibility that the trajectory (emission axis line) of the electron beams EB when being emitted from the electron gun 2 may not match the central axis line of the guide part 10 (particularly, the rod portion 10b) and may intersect the central axis line. Particularly, the electron gun 2 has a structure in which the filament 7 that emits electrons or the grid part 8 is held by the insulating block 5 formed from an insulating material such as an insulating resin and ceramic. Accordingly, an individual difference caused by the insulating block 5 also occurs, and thus it is very difficult to perform the processing, the assembly, the disposition, and the like with high accuracy. That is, in the electron gun 2, when the electron beams EB are emitted from the electron gun 2, if the trajectory of the electron beams EB is not adjusted, the electron beams EB is highly likely to be incident, for example, to an inner wall of the guide part 10 and the like before reaching the electron beam emission window 11. Therefore, the electron gun 2 has a configuration in which the electron beam amount emitted from the electron beam emission window 11 decreases (the electron beam amount that cannot reach the electron beam emission window 11 increases). Accordingly, with the electron gun 2 alone, it cannot be said that formation in the vacuum space Z, dimension fitting, and positioning are performed so that the electron beams EB pass through the guide part 10 and are emitted from the electron beam emission window 11.

Accordingly, in the electron beam irradiation device 1a, the adjustment electromagnetic coil 13 is disposed on the base end side of the guide part 10 at the outside of the vacuum space Z. When the trajectory of the electron beams EB in the guide part 10 is adjusted by the adjustment electromagnetic coil 13, high accuracy relating to the processing, the assembly, and the disposition of the electron gun 2 is not necessary, and it is possible to allow the electron beams EB emitted from the electron gun 2 to reliably reach the electron beam emission window 11 on the tip end side of the guide part 10, and emitting the electron beams therefrom. That is, it is possible to emit the electron beams EB from the electron beam emission window 11 with high efficiency due to the adjustment electromagnetic coil 13. In addition, when the adjustment electromagnetic coil 13 is disposed on an outside the vacuum space Z, it is possible to suppress a problem related to a decrease in the degree of vacuum of the vacuum space Z due to gas discharge from the adjustment electromagnetic coil 13, and thus it is possible to emit the electron beams EB from the electron beam emission window 11 with higher efficiency. In addition, it can also be considered that the adjustment electromagnetic coil 13 is disposed on the tip end side of the guide part 10, that is, a region of the rod portion 10b. However, in this case, it is very difficult to set the rod portion 10b provided with the adjustment electromagnetic coil 13 to a size capable of being inserted into the bottle B. It is preferable that a configuration of controlling the electron beam EB is not added to the rod portion 10b, and the control is performed at the base end portion 10a in front of the rod portion 10b.

Accordingly, according to the electron beam irradiation device 1a of this embodiment, the guide part 10 including the long tubular member capable of being inserted into the bottle B from the mouth portion Ba of the bottle B is provided, and thus it is possible to stably emit the electron beams EB from the electron beam emission window 11 on the tip end side of the guide part 10. In addition, a margin is provided in the degree of accuracy necessary for the electron gun 2, and thus it is easy to manufacture an electron beam irradiation device having an improved yield and uniform characteristics. In addition, the electron beams EB emitted from the electron gun 2 always enter an effective diameter range of the electron beam emission window 11, and thus it is possible to stably obtain a high-performance sterilization effect.

In the electron beam irradiation device 1a, as the adjustment part that adjusts the trajectory of the electron beams EB, the adjustment electromagnetic coil 13 that is an electromagnetic coil is provided. According to this, it is possible to finely adjust the trajectory of the electron beams EB in the guide part 10 by adjusting a current supplied to the adjustment electromagnetic coil 13, and thus it is possible to stably emit the electron beams EB from the electron beam emission window 11 on the tip end side of the guide part 10. In addition, it is also possible to easily countermeasure a variation in the trajectory of the electron beams EB which is caused by a variation with the passage of time due to thermal expansion and the like.

The electron beam irradiation device 1a further includes the focusing electromagnetic coil 14 that is disposed at the outside of the vacuum space Z and controls focusing of the electron beams EB as a focusing part. According to this, the focusing control of the electron beams EB in the guide part 10 is reliably performed, and thus it is possible to stably emit the electron beams EB from the electron beam emission window 11 on the tip end side of the guide part 10. In addition, as described above, the focusing electromagnetic coil 14 is provided as the focusing part, and thus it is possible to finely adjust focusing of the electron beams EB in the guide part 10 by adjusting a current supplied to the focusing electromagnetic coil 14. Accordingly, it is possible to more stably emit the electron beams EB from the electron beam emission window 11 on the tip end side of the guide part 10. More specifically, a deviation occurs in an irradiation range of the electron beams EB on the electron beam emission window 11 even when using the same focusing lens due to a deviation in processing, assembly, and disposition of the electron gun 2. As a result, it is difficult to make the electron beams EB emitted from the electron beam emission window 11 be uniform. In contrast, since the focusing electromagnetic coil 14 is set as the focusing part, it is possible to appropriately adjust the focusing lens through adjustment of a current that is supplied, and thus a deviation in an irradiation range of the electron beams EB on the electron beam emission window 11 is suppressed. Accordingly, it is possible to make the electron beams EB emitted from the electron beam emission window 11 be uniform. In addition, since the focusing electromagnetic coil 14 is disposed on an outside the vacuum space Z, it is possible to suppress a problem related to a decrease in the degree of vacuum of the vacuum space Z due to gas discharge from the focusing electromagnetic coil 14, and thus it is possible to emit the electron beams EB from the electron beam emission window 11 with higher efficiency.

However, in a case where the focusing point of the electron beams EB exists inside the guide part 10, the focusing point is located on the electron beam emission window 11, for example, due to an influence of discharging, and thus energy of the electron beams EB concentrates to a local site of the electron beam emission window 11. As a result, there is a concern that the electron beam emission window 11 may be broken. In contrast, in the electron beam irradiation device 1a, the electron beams EB are focused so that the focusing point is not formed inside the guide part 10 (particularly, the rod portion 10b) due to the focusing electromagnetic coil 14. According to this, it is possible to reduce the possibility of breakage of the electron beam emission window 11, and thus it is possible to stably emit the electron beams EB from the electron beam emission window 11 on the tip end side of the guide part 10.

In the electron beam irradiation device 1a, the adjustment electromagnetic coil 13 is disposed closer to the base end side of the guide part 10 than the focusing electromagnetic coil 14. According to this, the electron beams EB, which propagate toward the electron beam emission window 11 at the inside of the guide part 10, is subjected to the focusing control by the focusing electromagnetic coil 14 after the trajectory is finely adjusted by the adjustment electromagnetic coil 13. According to this, even in a case where a deviation in the trajectory of the electron beams EB from the electron gun 2 is great, it is possible to adjust the trajectory of the electron beams EB to be a trajectory capable of reliably performing the focusing control of the electron beams EB by the focusing electromagnetic coil 14. Accordingly, it is possible to stably emit the electron beams EB from the electron beam emission window 11 on the tip end side of the guide part 10. In addition, since it is possible to reliably perform the focusing control of the electron beams EB, it is possible to make the electron beams EB emitted from the electron beam emission window 11 be uniform.

In addition, in the electron beam irradiation device 1a, the adjustment electromagnetic coil 13 and the focusing electromagnetic coil 14 are provided on an outer side of the vacuum space Z, and a control magnetic field is introduced through the guide part 10. According to this, the following effect is exhibited. That is, it is possible to suppress a problem related to a decrease in the degree of vacuum of the vacuum space Z due to gas discharge from the adjustment electromagnetic coil 13 and the focusing electromagnetic coil 14. According to this, it is possible to emit the electron beams EB from the electron beam emission window 11 with higher efficiency. In addition, it is not necessary for the adjustment electromagnetic coil 13 and the focusing electromagnetic coil 14 to correspond to each other in vacuo, and thus simplification of a structure becomes possible. In addition, position adjustment of the adjustment electromagnetic coil 13 and the focusing electromagnetic coil 14 becomes easy.

In the electron beam irradiation device 1a, the electron beams EB can be adjusted to an arbitrary size on the electron beam emission window 11 by the focusing electromagnetic coil 14. It is possible to perform the focusing control of the electron beams EB by the focusing electromagnetic coil 14. Accordingly, in a case of changing the length L of the rod portion 10b of the guide part 10 or the effective diameter of the electron beam emission window 11, it is possible to correspond to the changing by replacing only the guide part 10 (rod portion 10b).

Next, a second embodiment will be described. In description of this embodiment, description will be given of a configuration different from that of the first embodiment, and redundant description will be omitted.

Figure 3:
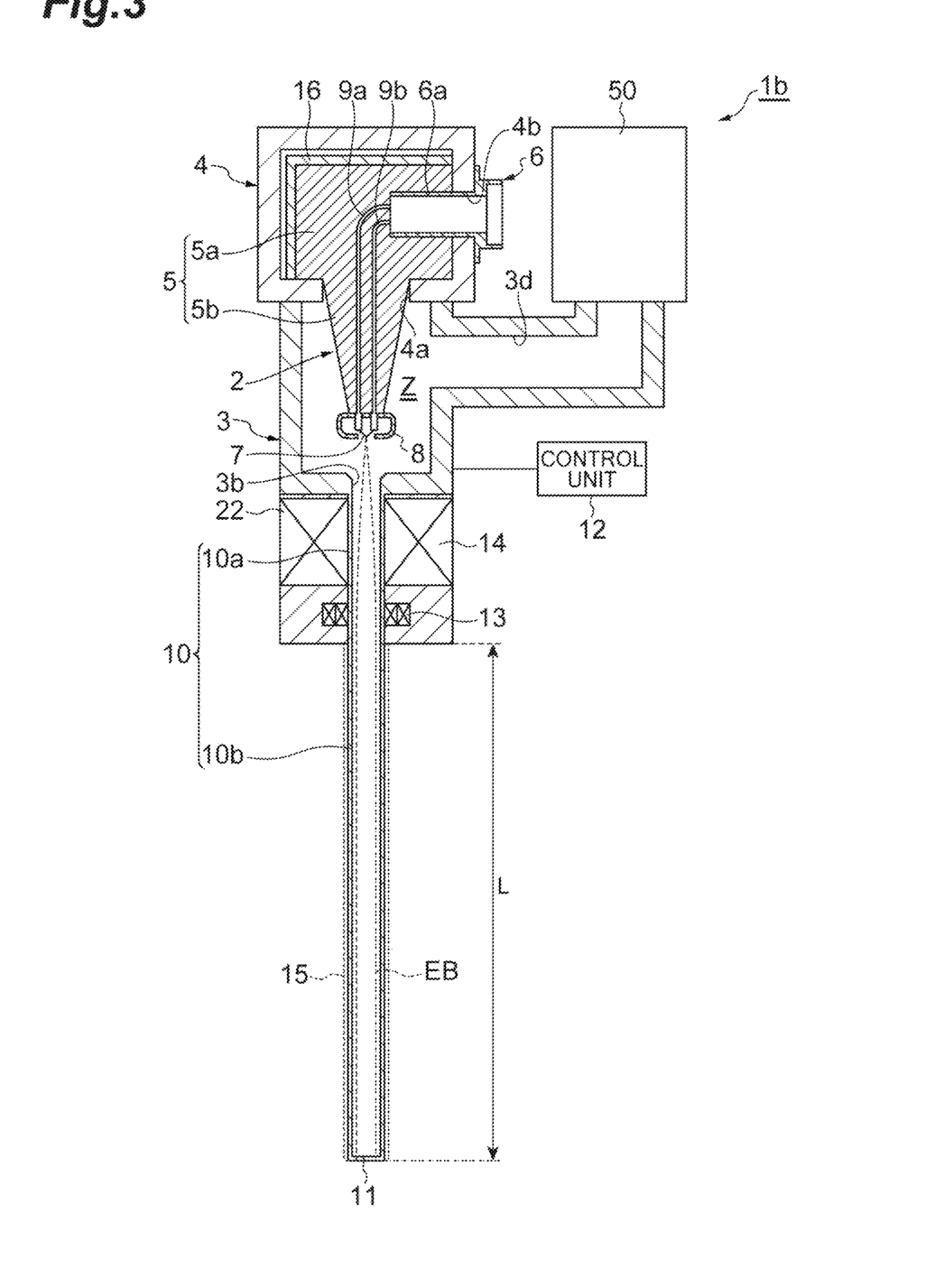
FIG. 3 is a cross-sectional view illustrating an electron beam irradiation device according to a second embodiment.

FIG. 3 is a longitudinal cross-sectional view of an electron beam irradiation device according to the second embodiment. An electron beam irradiation device 1b illustrated in FIG. 3 according to the second embodiment is different from the electron beam irradiation device 1a (refer to FIG. 1) in that disposition of the adjustment electromagnetic coil 13 and disposition of the focusing electromagnetic coil 14 is switched from each other.

The focusing electromagnetic coil 14 is provided to surround the base end portion 10a at a position on the base end side, which is adjacent to the vacuum container 3, in the base end portion 10a of the guide part 10. In the base end portion 10a of the guide part 10, the adjustment electromagnetic coil 13 is provided at a position adjacent to the front side (the tip end side of the guide part 10) with respect to the focusing electromagnetic coil 14. The focusing electromagnetic coil 14 and the adjustment electromagnetic coil 13 are disposed at the periphery of the base end portion 10a of the guide part 10 to be arranged in this order along the emission direction of the electron beams EB.

Even in the electron beam irradiation device 1b described above, the same effect as the effect in the electron beam irradiation device 1a is exhibited. In addition, in the electron beam irradiation device 1b, the focusing electromagnetic coil 14 is disposed closer to the base end side (electron gun 2 side) of the guide part 10 than the adjustment electromagnetic coil 13. According to this, the electron beams EB, which propagate toward the electron beam emission window 11 in the guide part 10, are subjected to the focusing control by the focusing electromagnetic coil 14, and then the trajectory of the electron beams EB is finely adjusted by the adjustment electromagnetic coil 13. Accordingly, even when divergence of the electron beams EB from the electron gun 2 is great, the trajectory of the electron beams EB is finely adjusted after focusing the divergence in advance, and thus it is possible to easily adjust the trajectory of the electron beam EB in the adjustment electromagnetic coil 13. It is possible to stably emit the electron beams EB from the electron beam emission window 11 on the tip end side of the guide part 10.

The invention is not limited to the above-described embodiments, and modifications can be made in a range not departing from the gist described in the appended claims, and other applications are also possible.

Figure 4:
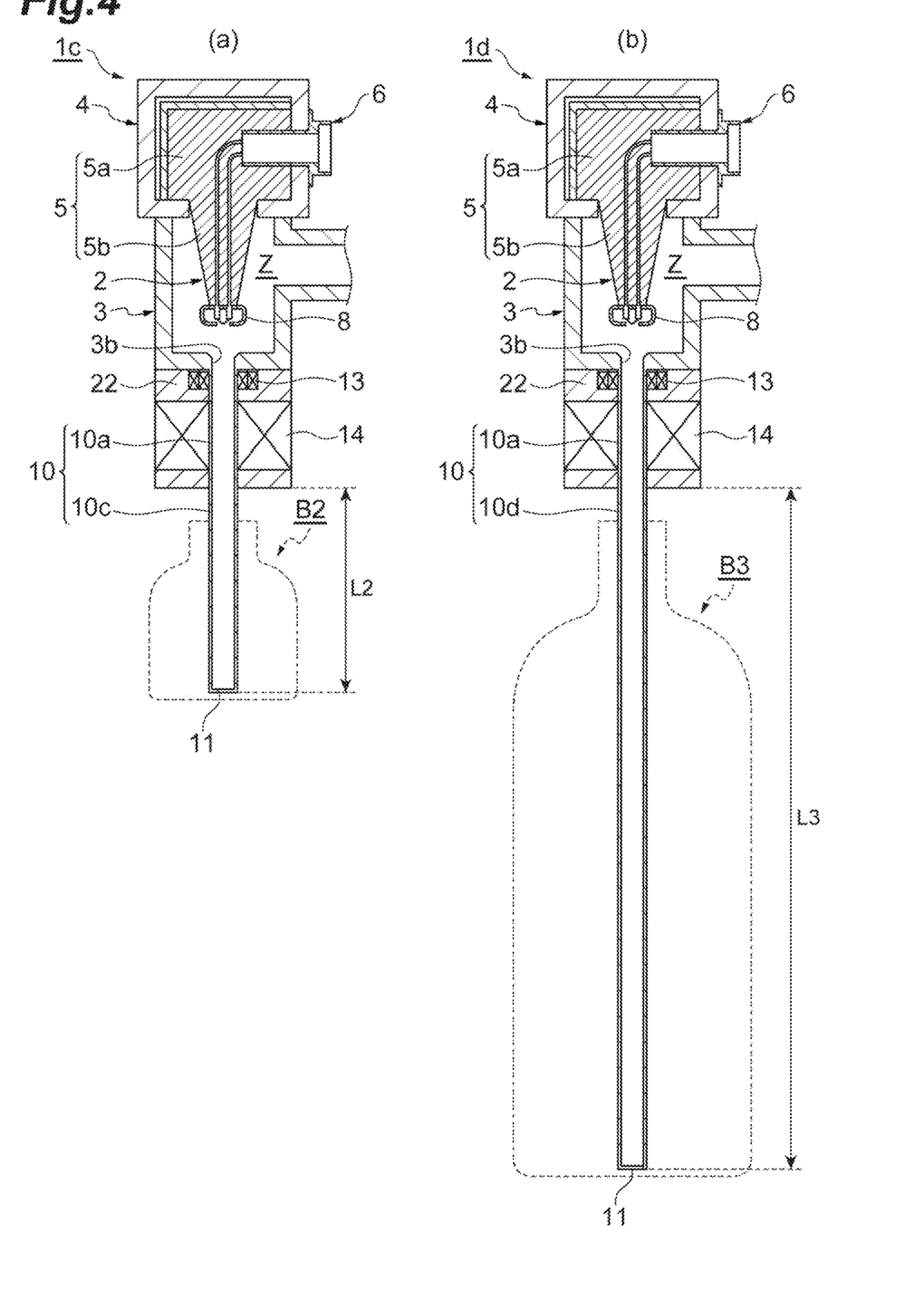
FIG. 4(a) is a cross-sectional view illustrating an electron beam irradiation device according to a modification example.
FIG. 4(b) is a cross-sectional view illustrating an electron beam irradiation device according to another modification example.

In the above-described embodiments, a length of the guide part 10 can be appropriately changed as long as the rod portion 10b on the tip end side can be inserted into the bottle B. For example, as in an electron beam irradiation device 1c illustrated in FIG. 4(a), a rod portion 10c having a length L2 smaller than the length L1 of the rod portion 10b may be provided. For example, the electron beam irradiation device 1c is used in a state in which the rod portion 10c is inserted into a bottle B2 having a height lower than that of the bottle B. In addition, in contrast, as in an electron beam irradiation device 1d illustrated in FIG. 4(b), a rod portion 10d having a length L3 longer than the length L of the rod portion 10b may be provided. For example, the electron beam irradiation device 1d is used in a state in which the rod portion 10d is inserted into a bottle B3 having a height greater than that of the bottle B.

In the above-described embodiments, the adjustment electromagnetic coil 13 is applied as the adjustment part, but the adjustment part is not particularly limited. Various kinds of units are applicable as the adjustment part as long as the trajectory of the electron beams EB can be adjusted. In the above-described embodiments, the focusing electromagnetic coil 14 is applied as the focusing part, but the focusing part is not particularly limited. Various kinds of units are applicable as the focusing part as long as the focusing control of the electron beams EB can be performed. In addition, the focusing part may not be provided.

REFERENCE SIGNS LIST 1a, 1b, 1c, 1d Electron beam irradiation device
2 Electron gun (electron beam generation part)
3 Vacuum container (housing part)
10 Guide part (electron beam guide part)
10a Base end portion
10b, 10c, 10d Rod portion
11 Electron beam emission window
13 Adjustment electromagnetic coil (adjustment part)
14 Focusing electromagnetic coil (focusing part)
B Bottle
Ba Mouth portion
EB Electron beam
Z Vacuum space

The invention claimed is:
1. An electron beam irradiation device, comprising:
an electron beam generation part that generates electron beams;
a housing part that provides a vacuum space in which the electron beam generation part is accommodated;
an electron beam guide part in which a base end side is connected to the housing part and communicates with the vacuum space, in which a tip end side is provided with a long tubular member capable of being inserted into a container via a mouth portion of the container, and in which the electron beams generated in the electron beam generation part pass through an inside;
an electron beam emission window which is provided on the tip end side of the electron beam guide part, and through which the electron beams are emitted; and
an adjustment part that adjusts a trajectory of the electron beams in the electron beam guide part,
wherein the adjustment part is disposed on the base end side of the electron beam guide part on an outside of the vacuum space, and
wherein the adjustment part is disposed between the electron beam generation part and the tubular member to surround the base end side of the electron beam guide part.

2. The electron beam irradiation device according to claim 1,
wherein the adjustment part is an electromagnetic coil.

3. The electron beam irradiation device according to claim 1, further comprising:
a focusing part that is disposed on an outside the vacuum space, and controls focusing of the electron beams in the electron beam guide part.

4. The electron beam irradiation device according to claim 3,
wherein the focusing part is an electromagnetic coil.

5. The electron beam irradiation device according to claim 3,
wherein the focusing part focuses the electron beams so that a focusing point is not formed on the inside of the electron beam guide part.

6. The electron beam irradiation device according to claim 3,
wherein the adjustment part is disposed closer to the base end side of the electron beam guide part than the focusing part.

7. The electron beam irradiation device according to claim 3,
wherein the focusing part is disposed closer to the base end side of the electron beam guide part than the adjustment part.

8. The electron beam irradiation device according to claim 1,
wherein the electron beam generation part is configured so that an electron beam amount of the electron beams emitted from the electron beam emission window of the tip end side of the electron beam guide part is reduced in a case where the adjustment part is not provided in comparison to a case where the adjustment part is provided.

9. An electron beam irradiation device, comprising:
an electron beam generation part that generates electron beams;
a housing part that provides a vacuum space in which the electron beam generation part is accommodated;
an electron beam guide part in which a base end side is connected to the housing part and communicates with the vacuum space, in which a tip end side is provided with a long tubular member capable of being inserted into a container via a mouth portion of the container, and in which the electron beams generated in the electron beam generation part pass through an inside;

an electron beam emission window which is provided on the tip end side of the electron beam guide part, and through which the electron beams are emitted;

an adjustment part that adjusts a trajectory of the electron beams in the electron beam guide part;

a focusing part that is disposed on an outside the vacuum space, and controls focusing of the electron beams in the electron beam guide part; and a control unit that controls the focusing part, wherein the adjustment part is disposed on the base end side of the electron beam guide part on an outside of the vacuum space, and the focusing part is an electromagnetic coil in which flows a current controlled by the control unit so as to perform a focusing control to suppress scattering of the electron beams while focusing the electron beams so that a focusing point is not formed on the inside of the electron beam guide part, and to make an irradiation range of the electron beams on the electron beam emission window constant.

10. The electron beam irradiation device according to claim 9, wherein the adjustment part is an electromagnetic coil.

11. The electron beam irradiation device according to claim 9, wherein the adjustment part is disposed closer to the base end side of the electron beam guide part than the focusing part.

12. The electron beam irradiation device according to claim 9, wherein the focusing part is disposed closer to the base end side of the electron beam guide part than the adjustment part.

13. A method of irradiating an inner surface of a container with electron beams by using an electron beam irradiation device including an electron beam generation part that generates the electron beams, a housing part that provides a vacuum space in which the electron beam generation part is accommodated, an electron beam guide part in which a base end side is connected to the housing part and communicates with the vacuum space, in which a tip end side is provided with a long tubular member capable of being inserted into a container via a mouth portion of the container on the tip end side, and in which the electron beams generated in the electron beam generation part pass through an inside, an electron beam emission window which is provided on the tip end side of the tubular member of the electron beam guide part, and through which the electron beams are emitted, an adjustment part that is disposed on the base end side of the electron beam guide part on an outside of the vacuum space, and adjusts a trajectory of the electron beams in the electron beam guide part, and a focusing part that controls focusing of the electron beams in the electron beam guide part, the method comprising:

a step of generating the electron beams from the electron beam generation part, and adjusting a trajectory of the electron beams passing through the electron beam guide part by the adjustment part while allowing the electron beams to pass through the inside of the electron beam guide part, thereby allowing the electron beams to reach the electron beam emission window and emitting the electron beams therefrom; and a step of setting the electron beams to an emission state, then inserting the tubular member into the inside of the container via the mouth portion of the container, and irradiating the inner surface of the container with the electron beams while constantly varying a relative positional relationship between the container and the electron beam emission window, wherein the irradiating step with the electron beams includes a step of positioning the tip end of the tubular member on the inside of the container, and irradiating a bottom surface of the container with the electron beams, and the emitting step includes adjusting the trajectory of the electron beams by the adjustment part to match with the central axis line of the tubular member, and focusing the electron beams by the focusing part so that a focusing point is not formed on the inside of the electron beam guide part.

* * * * *